(12) United States Patent
Delalande et al.

(10) Patent No.: US 12,077,744 B2
(45) Date of Patent: Sep. 3, 2024

(54) DEVICE FOR DISPENSING MICROBUBBLES FOR CELL SONOPORATION

(71) Applicants: CENTRE NATIONAL DE LA RECHERCHE SCIENTIFIQUE (CNRS), Paris (FR); UNIVERSITE D'ORLEANS, Orleans (FR)

(72) Inventors: Anthony Delalande, Sandillon (FR); Matthias Lebertre, Tours (FR); Michaël Delalande, Grenoble (FR); Chantal Pichon, Saint Denis de l'Hotel (FR)

(73) Assignees: CENTRE NATIONAL DE LA RECHERCHE SCIENTIFIQUE (CNRS), Paris (FR); UNIVERSITE D'ORLEANS, Orleans (FR)

( * ) Notice: Subject to any disclaimer, the term of this patent is extended or adjusted under 35 U.S.C. 154(b) by 840 days.

(21) Appl. No.: 17/277,351

(22) PCT Filed: Sep. 18, 2019

(86) PCT No.: PCT/EP2019/075075
§ 371 (c)(1),
(2) Date: Mar. 18, 2021

(87) PCT Pub. No.: WO2020/058367
PCT Pub. Date: Mar. 26, 2020

(65) Prior Publication Data
US 2022/0033756 A1    Feb. 3, 2022

(30) Foreign Application Priority Data

Sep. 18, 2018 (FR) ...................................... 1858385

(51) Int. Cl.
*C12M 1/42* (2006.01)
*A61B 8/00* (2006.01)
(Continued)

(52) U.S. Cl.
CPC ............. *C12M 35/04* (2013.01); *A61B 8/445* (2013.01); *A61M 37/0092* (2013.01);
(Continued)

(58) Field of Classification Search
CPC ...... C12N 15/87; C12N 15/8206; C12M 1/42; C12M 35/04; C12M 41/48; A61B 17/22;
(Continued)

(56) References Cited

U.S. PATENT DOCUMENTS 5,141,131 A    8/1992  Miller, Jr. et al.
5,558,092 A *  9/1996  Unger .................. A61B 8/0833
                                                              601/3
(Continued)

FOREIGN PATENT DOCUMENTS

CN         102036755 A      4/2011
CN         202610237 U     12/2012
WO      WO-2015110955 A1    7/2015

*Primary Examiner* — Scott A Smith
(74) *Attorney, Agent, or Firm* — Panitch Schwarze Belisario & Nadel LLP; Erin M. Dunston

(57) ABSTRACT

The invention describes a device (10) for dispensing microbubbles (30) for cell sonoporation, comprising:
a tube configured to receive a vial (20) containing a solution (26) of microbubbles (30),
at least two catheters (11, 12) arranged inside the tube and opening into the vial (20) when the latter is received by the tube,
wherein, when the first catheter (11) is connected to a first air injection source, air can be injected into the vial (20) via the first catheter so as to generate an overpressure therein, the microbubbles (30) contained in the vial (20) entering the second catheter (12) and moving toward its second end (122). The invention also relates to a sonoporation device, a sonoporation process and a computer program product.

14 Claims, 5 Drawing Sheets

(51) Int. Cl.
*A61M 37/00* (2006.01)
*C12M 1/36* (2006.01)
*C12N 15/87* (2006.01)
*A61B 8/08* (2006.01)
*A61B 17/22* (2006.01)

(52) U.S. Cl.
CPC .............. *C12M 1/42* (2013.01); *C12M 41/48* (2013.01); *C12N 15/87* (2013.01); *A61B 8/0816* (2013.01); *A61B 8/4483* (2013.01); *A61B 17/22* (2013.01)

(58) Field of Classification Search
CPC . A61B 17/2202; A61B 8/0808; A61B 8/0816; A61B 8/0833; A61B 8/12; A61B 8/445; A61B 8/4483; A61B 8/481; A61M 25/00; A61M 37/00; A61M 37/0092
USPC ............ 600/411, 437, 439, 458; 604/22, 23, 604/890.1
See application file for complete search history.

(56) References Cited

U.S. PATENT DOCUMENTS

| | | | | |
|---|---|---|---|---|
| 5,752,515 | A * | 5/1998 | Jolesz | A61B 8/0808 600/458 |
| 6,428,477 | B1 * | 8/2002 | Mason | G01S 15/899 601/3 |
| 6,716,168 | B2 * | 4/2004 | Nock | A61M 37/0092 604/890.1 |
| 7,338,451 | B2 * | 3/2008 | Tsuzuki | G01S 7/52038 600/458 |
| 2009/0270790 | A1 * | 10/2009 | Raghavan | A61M 37/00 604/22 |
| 2010/0143241 | A1 | 6/2010 | Johnson et al. | |
| 2011/0057988 | A1 * | 3/2011 | Izumikawa | G03G 15/2096 347/21 |
| 2012/0209116 | A1 * | 8/2012 | Hossack | A61M 25/00 604/23 |
| 2016/0067367 | A1 * | 3/2016 | Jin | A61L 9/125 239/152 |
| 2022/0033756 | A1 * | 2/2022 | Delalande | C12N 15/87 |

* cited by examiner

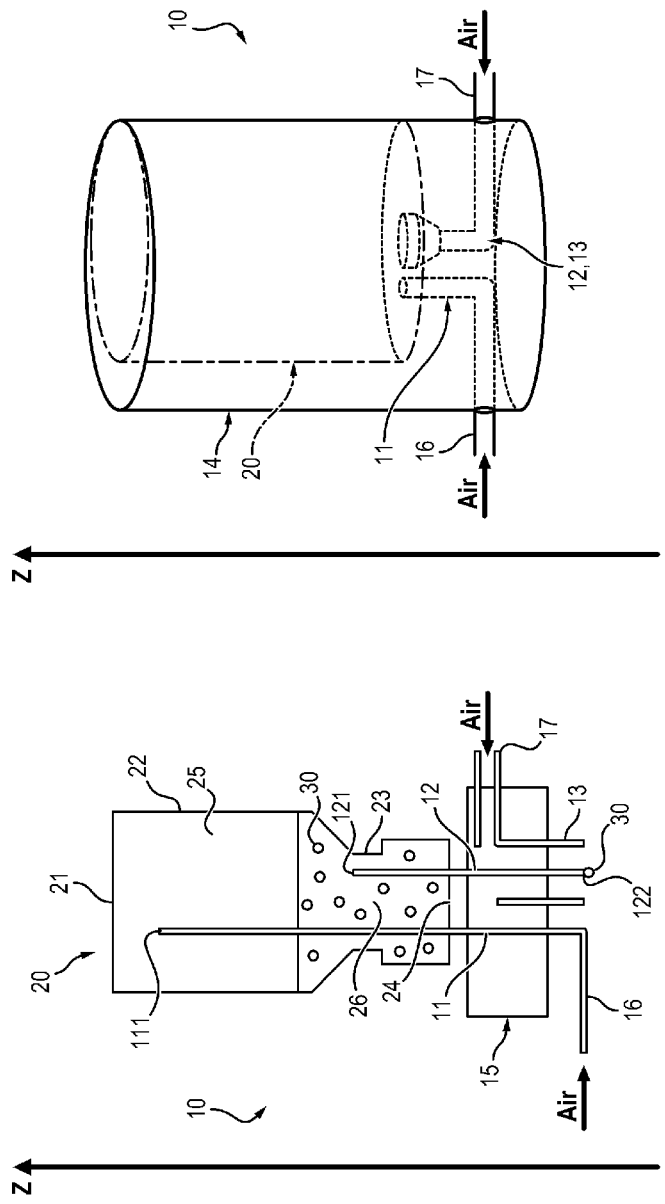

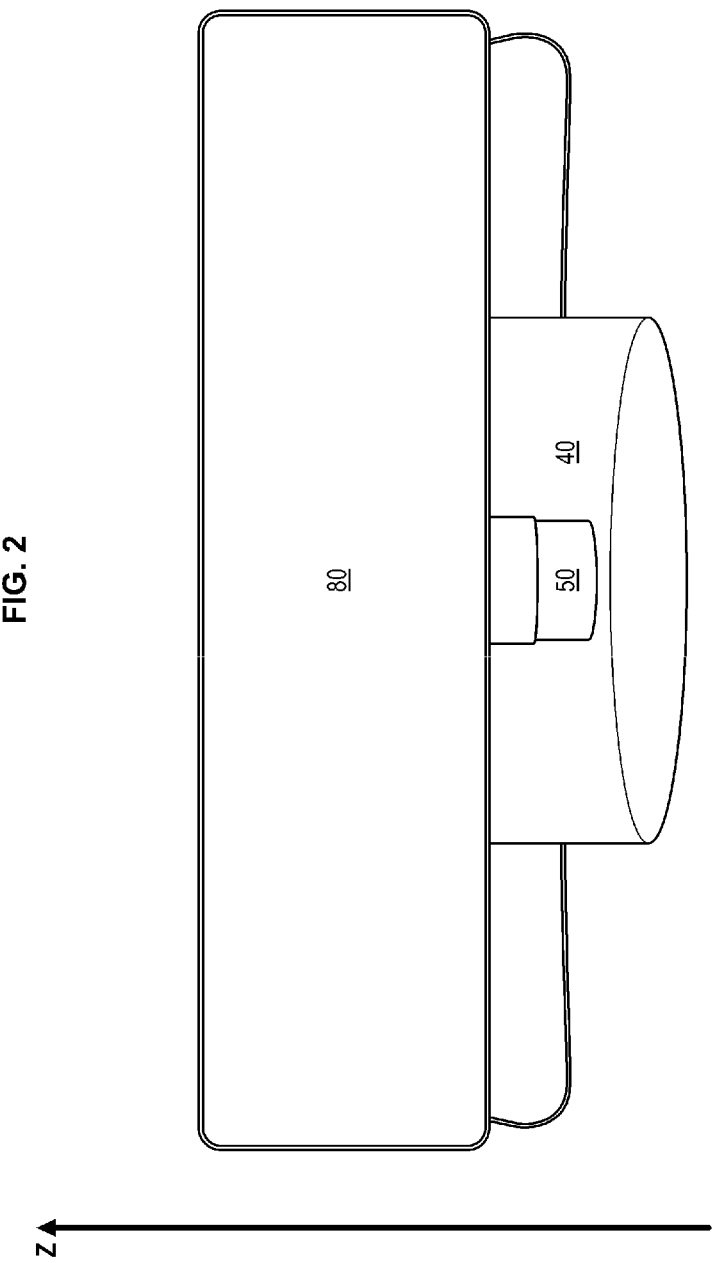

DEVICE FOR DISPENSING MICROBUBBLES FOR CELL SONOPORATION

CROSS-REFERENCE TO RELATED APPLICATIONS

This application is a U.S. National Stage Application pursuant to 35 U.S.C. § 371 of International Patent Application PCT/EP2019/075075, filed on Sep. 18, 2019, and published as WO 2020/058367 on Mar. 26, 2020, which claims priority to French Patent Application 1858385, filed on Sep. 18, 2018, all of which are incorporated herein by reference in their entireties for all purposes.

FIELD OF THE INVENTION

The present invention relates to the field of cell transfection, in particular sonoporation using microbubbles. The invention relates more particularly to a device for dispensing microbubbles, as well as to a process for cell sonoporation by means of such a device.

BACKGROUND ART

Cell transfection is a method consisting in introducing active molecules (such as nucleic acids, chemotherapeutic molecules, markers, proteins, etc.) into cells to be transfected, without resorting to viruses, as opposed to transduction.

Cell sonoporation is a transfection method consisting of using ultrasonic waves to modify the permeability of cells, so as to allow the introduction of active molecules into the cells to be transfected.

A known type of sonoporation device is for example described in document WO 2015/110955. This device comprises an ultrasonic transducer placed at the bottom of a tank filled with a liquid and emitting ultrasonic waves to cells to be transfected placed on a mobile structure.

In a known way, the efficiency of the sonoporation operation can be greatly improved by encapsulating the active molecules in microbubbles. The microbubbles containing the active molecules are then brought into contact with the cells to be transfected and vibrate under the effect of the ultrasonic waves emitted by the transducer. Their interactions with the cells to be transfected permeabilize the membranes of the latter, allowing the active molecules to enter the cells to be transfected.

One problem is that the dispensing of the microbubbles over the cells to be transfected is carried out manually by a user using a micropipette. Such dispensing is tedious and leads to poor efficiency of the sonoporation operation.

SUMMARY OF THE INVENTION

One goal of the invention is to propose a device for dispensing microbubbles for cell sonoporation with improved efficiency compared with devices of known type.

According to a first aspect, the invention relates to a device for dispensing microbubbles for cell sonoporation, characterized in that the device comprises:
  a tube symmetrical about a vertical axis, said tube being configured to receive a vial containing a solution of microbubbles,
  at least two catheters arranged inside the tube, said catheters being at least partially oriented substantially parallel to the vertical axis, each of the catheters having at a first end an orifice adapted to open into the vial when the latter is received by the tube, the first catheter being adapted to be connected to a first air injection source, the second catheter having a second end,
  wherein, when the first catheter is connected to the first air injection source, air can be injected into the vial via the orifice of the first catheter, the injected air generating an overpressure in the vial, so that microbubbles contained in the vial enter the second catheter via the orifice of its first end and then move inside the second catheter toward its second end.

Such a device is capable of dispensing a precise and controlled quantity of microbubbles automatically, without requiring manual operation on the part of the user. The device provides improved accuracy of microbubble dispensing location, the positions of the tube and catheters being fixed, unlike the case where the user must hold the pipette containing the microbubbles by hand.

Such a device therefore leads to improved microbubble dispensing efficiencies.

Furthermore, such a dispensing of microbubbles does not require contact with the microbubbles, which, during sonoporation, protects the cells from any biological contamination.

The microbubble dispensing device may comprise a third catheter at least partially located around at least part of the second catheter, the third catheter being adapted to be connected to a second air injection source. This third catheter makes it possible, via the second air injection source, to detach the microbubbles that have moved to the second end of the second catheter to dispense them to cells to be transfected. The deposition of microbubbles with this third catheter is faster and more precise.

The invention also relates to a cell sonoporation device comprising such a device for dispensing microbubbles.

The sonoporation device may comprise a first air injection source connected to the first catheter. This first air injection source allows air to be injected into the vial received by the microbubble dispensing device, in order to force microbubbles through the second catheter and move them to the second end of the second catheter.

The sonoporation device may optionally comprise a second air injection source connected to the third catheter, when the device for dispensing microbubbles comprises a third catheter. In this way, the microbubbles that have moved to the second end of the second catheter can be detached from it automatically and precisely, to be dispensed to the cells to be transfected.

The cell sonoporation device may further comprise:
  a tank intended to be at least partially filled with a liquid,
  an ultrasonic transducer arranged inside the tank,
  a plate comprising at least one receptacle intended to receive cells to be transfected,
  a mobile support adapted to receive the plate,
  a mobile support moving unit, configured to move the support.

With such a cell sonoporation device, the cells to be transfected can be moved relative to the microbubble dispensing device and to the ultrasonic transducer. The accuracy of microbubble dispensing is therefore improved, which contributes to improved sonoporation efficiencies compared with known devices.

Some preferred but not limiting features of the cell sonoporation device are the following, taken individually or in combination:
  the moving unit comprises rails extending in at least two dimensions defining a plane perpendicular to the vertical axis, called horizontal plane, the third dimension being that of the vertical axis, the support being intended to be moved along said rails. Thus, the location of the plate containing the cells to be transfected with respect to the sonoporation device can be controlled, thus improving the accuracy of the location of the dispensed microbubbles.

the moving unit further comprises a motor adapted to move the support in at least two dimensions defining a plane perpendicular to the vertical axis, called horizontal plane, the third dimension being that of the vertical axis. In this way, the location of the plate containing the cells to be transfected in relation to the location of the sonoporation device can be controlled automatically, without the need for manual operation on the part of a user.

the device for dispensing microbubbles is positioned facing the ultrasonic transducer along the vertical axis. Thus, the cells to be transfected can be moved in relation to both the ultrasonic transducer and the device for dispensing microbubbles and can be placed on the same axis as these two elements, thus improving the efficiency of the sonoporation operation.

the sonoporation device further comprises a housing comprising a first part configured to house the possible air injection sources as well as at least part of the moving unit, the housing further comprising a second part configured to house the device for dispensing microbubbles, the tank, the ultrasonic transducer, the plate and the mobile support, the second part further comprising a cover adapted to be opened or closed, said cover in the open position allowing a user to access at least the plate. Such a housing can be used to contain the entire cell sonoporation device in a biosafety cabinet, and to improve its modularity. In the closed position, the cover limits evaporation, isolates the cells to be transfected and protects users from movement of the support. In the open position, a user can access certain elements of the device, which can thus be changed in a modular way and/or cleaned, facilitating maintenance of such a device.

The sonoporation device may further comprise a processing unit configured to control at least one of the following elements: device for dispensing microbubbles, ultrasonic transducer, moving unit, possible first air injection source and second air injection source, cover. Such a processing unit allows an automatic control of the microbubble dispensing sequence, the moving of the plate, the characteristics of the ultrasonic waves, as well as the parameters of the sonoporation operation.

According to a second aspect, the invention relates to a process of cell sonoporation by means of a device for dispensing microbubbles according to the first aspect, a vial containing a solution of microbubbles being received in the device for dispensing microbubbles, the sonoporation process comprising a step of injecting air into the vial via the orifice of the first end of the first catheter, the injected air generating an overpressure in the vial, so that microbubbles contained in the vial enter the second catheter via the orifice of its first end and then move inside the second catheter toward its second end.

The sonoporation process may further comprise the following steps, taken individually or in combination:

a step of injecting air into a third catheter at least partially located around at least part of the second catheter, a step of moving the support wherein, with the device for dispensing microbubbles positioned facing the ultrasonic transducer along the vertical axis, the support is moved so as to successively place each receptacle of the plate between the device for dispensing microbubbles and the ultrasonic transducer along the vertical axis.

According to a third aspect, the invention relates to a computer program product comprising code instructions for the execution of a cell sonoporation process when this program is executed by a processor.

PRESENTATION OF FIGURES

Other aspects, goals and advantages of the present invention will appear upon reading the following detailed description, given by way of non-limiting example, which will be illustrated by the following figures:

FIGS. 1a and 1b are diagrams representing a device for dispensing microbubbles conforming to the invention.

FIG. 2 is a diagram representing a tank and an ultrasonic transducer for a sonoporation device conforming to the invention.

DETAILED DESCRIPTION OF AN EMBODIMENT

Microbubble Dispensing and Sonoporation Device

Figure 3A:
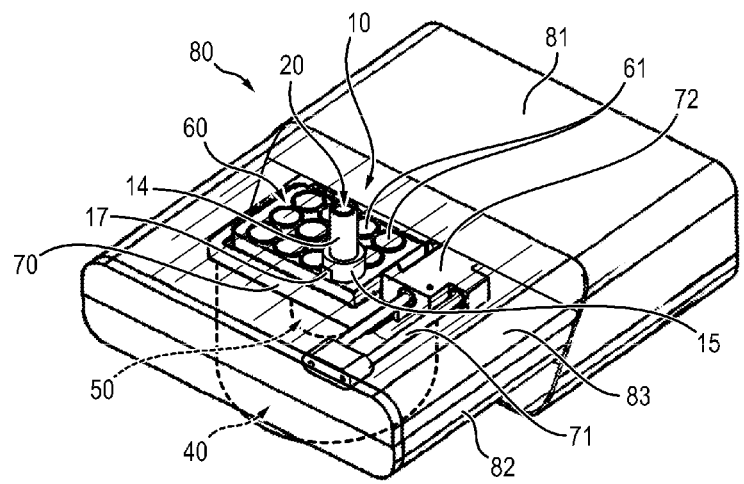
FIGS. 3a and 3b are diagrams representing a sonoporation device conforming to the invention, respectively in the closed and open positions of the cover.
Figure 3B:
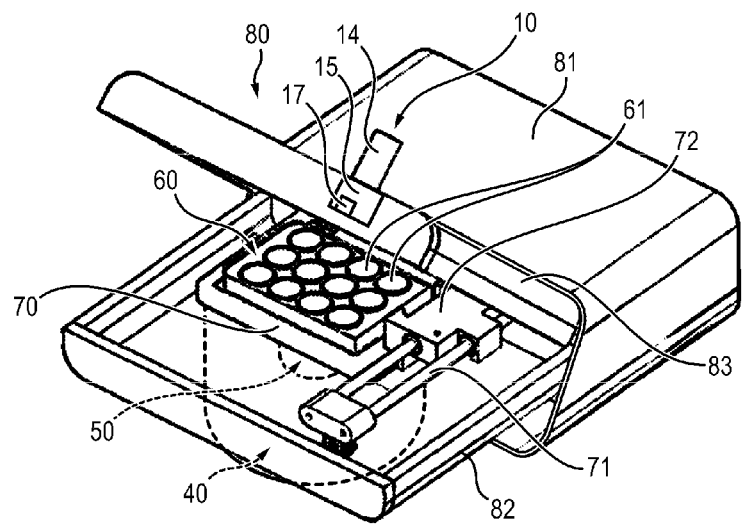
Figure 4:
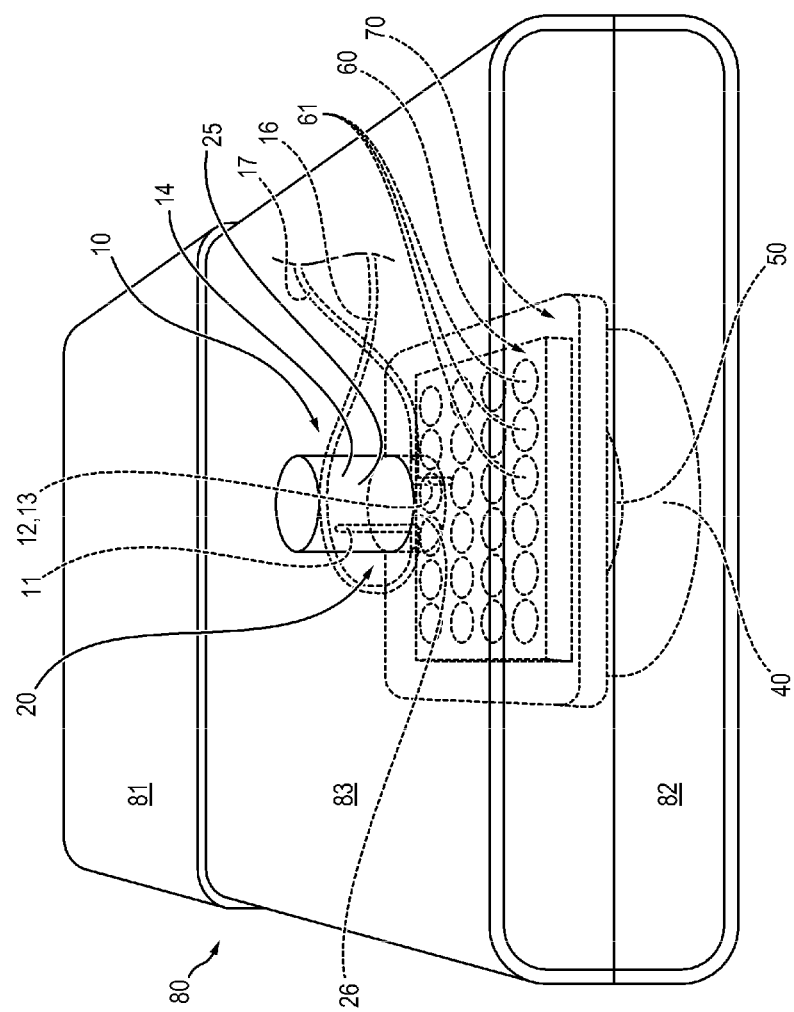
FIG. 4 is a diagram representing a sonoporation device conforming to the invention.

FIGS. 1a and 1b show a device 10 for dispensing microbubbles 30 for cell sonoporation.

The device 10 for dispensing microbubbles 30 comprises a tube 14. The tube 14 can be rigid, substantially cylindrical in shape, and rotationally symmetrical about a vertical axis Z.

The tube 14 defines a space adapted to receive a vial 20 containing a solution 26 of microbubbles 30. The diameter of the microbubbles 30 may vary according to the type of sonoporation to be performed.

The vial 20 can be a crimp vial. The vial 20 may have a bottom 21, a substantially cylindrical body 22, a neck 23 of smaller dimensions than the body 22, and a head 24 enlarged in relation to the neck 23, the head 24 preferably being closed by a septum.

The vial 20 is preferably positioned with the head 24 down in the tube 14 of the device 10 for dispensing microbubbles 30. Thus positioned, the head 24 of the vial 20, its neck 23 and part of its body 22 are filled with solution 26 containing the microbubbles 30. The part of the vial 20 which is not filled with the solution 26 is filled with air 25. The body 22 of the vial 20 can be in direct contact with the tube 14 of the device 10 for dispensing microbubbles 30. In a variant, a gap remains between the body 22 and the tube 14.

The device 10 for dispensing microbubbles 30 may also have a cylindrical lower part 15. The lower part 15 is rotationally symmetrical with respect to the vertical axis Z passing through the center of the tube 14, and can be in contact with the tube 14. The lower part 15 may have a larger diameter than the tube 14 intended to receive the vial 20.

The device 10 for dispensing microbubbles 30 comprises a first catheter 11. The first catheter 11 is fixed in the lower part 15 of the device 10 for dispensing microbubbles 30. The first catheter 11 may be substantially cylindrical in shape and rotationally symmetrical about the vertical axis Z.

The first catheter 11 has a first end 111, which has an orifice. When the vial 20 is received in the tube 14, the first catheter 11 pierces the septum of the vial 20 and the orifice of its first end 111 opens vertically into the vial 20, preferably into the air 25 contained in the vial 20.

The first catheter 11 is adapted to be connected to a first air injection source. The connection between the first air injection source and the first catheter 11 is made through a first air inlet pipe 16.

Thus, the air injected by the first air injection source passes through the first air inlet pipe 16 and then the first catheter 11, and is injected into the vial 20 via the orifice of the first end 111 of the first catheter 11, which creates an overpressure in the vial 20.

The device 10 for dispensing microbubbles 30 comprises a second catheter 12. The second catheter 12 is fixed in the lower part 15 of the device 10 for dispensing microbubbles 30. The second catheter 12 can be substantially cylindrical in shape and rotationally symmetrical about the vertical axis Z.

The second catheter 12 has a first end 121, which has an orifice. When the vial 20 is received in the tube 14, the second catheter 12 pierces the septum of the vial 20 and the orifice of its first end 121 opens vertically into the vial 20, preferably into the solution 26 of microbubbles 30 contained in the vial 20.

The second catheter 12 has a second end 122. The second end 122 of the second catheter 12 opens preferably outside the tube 14 and the lower part 15 of the device 10 for dispensing microbubbles 30.

Thus, the overpressure generated in the vial 20 pushes the microbubbles 30 contained in the vial 20 to enter the second catheter 12 via the orifice of its first end 121, and then to move inside the second catheter 12 toward its second end 122.

According to a preferred embodiment, the device 10 for dispensing microbubbles 30 comprises a third catheter 13. The third catheter 13 may be substantially cylindrical in shape and rotationally symmetrical about this vertical axis Z.

The third catheter 13 is located around at least part of the second catheter 12. The third catheter can be fixed and located inside the lower part 15 of the device 10 for dispensing microbubbles 30. One end of the third catheter 13 may open outside the tube 14 and the lower part 15 of the device 10 for dispensing microbubbles 30, and near the second end 122 of the second catheter 12.

The third catheter 13 is adapted to be connected to a second air injection source. The connection between the second air injection source and the third catheter 13 is made through a second air inlet pipe 17.

Thus, air can be injected through the second air injection source into the third catheter 13, the injected air detaching the microbubbles 30 that have moved to the second end 122 of the second catheter 12 to dispense them to the cells to be transfected.

According to a preferred embodiment, the device 10 for dispensing microbubbles 30 is fixed. In a variant, the device 10 for dispensing microbubbles 30 can comprise a moving unit allowing it to be moved, in particular in translation in one or more directions. Such a movement of the device 10 for dispensing microbubbles 30 contributes to the accuracy of the localization of the dispensing of the microbubbles 30.

The device 10 for dispensing microbubbles 30 can be used with anionic microbubbles 30, which are the most commonly used microbubbles 30 at present for cell sonoporation operations.

In a variant, the device 10 for dispensing microbubbles 30 can be used with cationic microbubbles 30. Such cationic microbubbles 30 are capable of electrostatic interactions with active molecules such as nucleic acids, which are anionic and then bind to the outside of the microbubbles 30. These cationic microbubbles 30 are obtained by adding lipids to the anionic microbubbles 30. They allow sonoporation efficiencies of the order of five times higher than those obtained with anionic microbubbles 30.

FIGS. 2, 3a, 3b and 4 represent cell sonoporation devices comprising devices for dispensing microbubbles 10 according to an embodiment.

The sonoporation device may also comprise a first air injection source connected to the first catheter 11. The sonoporation device may also comprise a second air injection source connected to the third catheter 13, when the device 10 for dispensing microbubbles 30 comprises a third catheter 13. The first and second air injection sources are, for example, pumps or compressors.

According to a preferred embodiment, the cell sonoporation device further comprises:
- a tank 40 intended to be at least partially filled with a liquid,
- an ultrasonic transducer 50 located inside the tank 40,
- a plate 60 comprising at least one receptacle 61 intended to receive cells to be transfected,
- a mobile support 70 adapted to receive the plate 60,
- a support 70 moving unit 71, 72 configured to move the support 70.

According to a preferred embodiment, the tank 40 is substantially cylindrical around the vertical axis Z. The tank 40 can be translucent and filled with a liquid, such as water, to propagate the ultrasonic waves from the transducer 50. The size of the tank 40 is adapted to the dimensions of the plate 60 and the support 70. The tank 40 can also comprise liquid level detection means, capable of verifying that the liquid level is sufficient to allow the proper propagation of ultrasonic waves in the tank 40. The tank 40 may also comprise a drain valve to allow the liquid it contains to be drained. Furthermore, the tank 40 may contain a seal, such as a double O-ring seal, to ensure a tight seal between the ultrasonic transducer 50 and the liquid it contains.

The ultrasonic transducer 50 is preferably fixed and located in the center of the tank 40. It can be located substantially in the middle of it. The ultrasonic transducer 50 is connected to a power source by a cable through an orifice of the tank 40. The ultrasonic transducer 50 can be interchanged, in order to adapt the characteristics of the ultrasonic waves as a function of, for example, the size of the microbubbles 30 used, the nature of the active molecules and/or the cells to be transfected, the desired efficiency and/or speed of the sonoporation operation, etc.

The plate 60 preferably extends in a plane perpendicular to the vertical axis Z, called horizontal plane. The plate 60 can have a substantially rectangular lower side and upper side with the same dimensions. The dimensions of the plate 60 can be adapted to be able to be contained within the enclosure of a biosafety cabinet. The plate 60 may have several receptacles 61 evenly distributed on its upper side, the receptacles 61 being intended to contain cells to be transfected. The receptacles 61 can be cylindrical, and extend along the vertical axis Z into the depth of the plate 60. The distance between the lower side of the plate 60 and the bottom of the receptacles 61 may be of the order of a millimeter. The plate 60 can be placed between the ultrasonic transducer 50 and the device 10 for dispensing microbubbles 30 along the vertical axis Z. The ultrasonic transducer 50 can be placed on the lower side of the plate 60, preferably at a fixed distance from it. The device 10 for dispensing microbubbles 30 can be placed on the upper side of the plate 60, preferably at a fixed distance from it.

The support 70 can have consistent dimensions of the plate 60 and extend all around it. The support 70 can fix the plate 60, for example by recessing it, or by means of fasteners such as screws.

The moving unit 71, 72 may comprise travel rails 71 extending in at least two dimensions defining a plane perpendicular to the vertical axis Z, called horizontal plane, the third dimension being that of the vertical axis Z. The moving unit 71, 72 may also comprise a moving element 72, adapted to slide along the rails 71. The mobile support 70 can be attached to the moving element 72, and moved along the rails 71 in translation in the horizontal plane and, if necessary, along the vertical axis Z.

The moving unit 71, 72 may further comprise one or more motors adapted to move the support 70 in at least one of the dimensions defined above. Thus, the movement of the support 70 can be carried out automatically by motors. In a variant, the moving unit 71, 72 can be equipped with manual means of movement, for example micrometer screws. In a variant, the moving unit can be equipped with both motors and manual means of movement. For example, the support 70 can be moved automatically by motors in the horizontal plane and manually with micrometer screws along the vertical axis Z.

According to a preferred embodiment, the device 10 for dispensing microbubbles 30 is positioned facing the ultrasonic transducer 50 along the vertical axis Z. The moving unit 71, 72 can then move the support 70, and thus the plate 60, so as to successively place each receptacle 61 between the ultrasonic transducer 50 and the device 10 for dispensing microbubbles 30 on the vertical axis Z. The microbubbles 30 once detached from the second end 122 of the second catheter 12 can then be dispensed to the receptacles 61 under the effect of gravity.

In the sonoporation device described in the preceding paragraphs, the vial 20 is located near the second end 122 of the second catheter 12, which is itself located near the receptacles 61 containing the cells to be transfected. Such a device limits the distance to be covered by the microbubbles 30 between the vial 20 and the cells to be transfected, and in particular limits the dimensions of the second catheter 12, which leads to higher sonoporation efficiencies.

In a variant, the vial 20 containing the microbubbles 30 can be positioned further away from the cells to be transfected, for example on one side of the device.

The sonoporation device may also comprise a power source capable of powering the ultrasonic transducer 50.

According to a preferred embodiment, the sonoporation device further comprises a housing 80. The tube 14 of the device 10 for dispensing microbubbles 30 can be attached to the housing 80 and protrude from it. Thus, the introduction of the vial 20 into the tube 14 can be carried out from outside the housing 80. In the case where the device 10 for dispensing microbubbles 30 comprises a moving unit, this moving unit can, for example, comprise travel rails attached to the housing 80, along which the device 10 for dispensing microbubbles 30 can move. The tube 14 of the device 10 for dispensing microbubbles 30 can then be attached to the rails instead of the housing 80.

In a variant, certain elements, for example the tank 40 and the ultrasonic transducer 50, or the device 10 for dispensing microbubbles 30, can be located outside the housing 80.

According to a preferred embodiment, the housing 80 consists of a first part 81 and a second part 82. The first part 81 can be opaque and the second part 82 can be transparent. The first part 81 may comprise the two air injection sources, the power source, the motor of the moving unit 71, 72, and some or all of the travel rails 71. The second part 82 may comprise the device 10 for dispensing microbubbles 30, the tank 40, the ultrasonic transducer 50, the plate 60 and its support 70, as well as some or all of the travel rails 71.

The second part 82 of the housing 80 can also comprise a cover 83 adapted to be opened or closed. The cover 83 can be transparent. In the closed position, the cover 83 limits evaporation, isolates the cells to be transfected and protects users from movement of the support 70. In the open position, a user can access certain elements of the device, such as the plate 60, the support 70, the tank 40 and its transducer 50. Thus, some elements can be changed in a modular way and/or cleaned, which facilitates the maintenance of such a device. Preferably, the cover 83 comprises closing means adapted to be operated automatically.

In a preferred embodiment, the cell sonoporation device further comprises a processing unit configured to control with software at least one of the following elements: device 10 for dispensing microbubbles 30, ultrasonic transducer 50, moving unit 71, 72, first air injection source and second air injection source, means of closing the cover 83.

The processing unit can be located inside or outside of the sonoporation housing 80. It can be connected, for example, by USB to a computer which has a man-machine interface allowing a user to control the sonoporation operation.

Such a processing unit automatically controls the characteristics of the dispensing of the microbubbles 30 (volume dispensed, position and time of dispensing, time between each dispensed microbubble 30, number of dispensing operations, etc.), the parameters of the ultrasonic waves (frequency, amplitude, power, transmission time, etc.), the movement of the support 70 (directions and speed of movement, position), the opening and closing of the cover 83, etc.

The sonoporation device described in the above paragraphs is intended for use in vitro. In a variant, the device can be used in vivo, with the sonoporation operation being controlled with the same processing unit as for in vitro use. The ultrasonic transducer 50 is then chosen to be compatible with amplitudes required for in vivo use, which are higher than those for in vitro use. The tank 40 can be chosen so that its dimensions are smaller than those of an in vitro sonoporation, and is placed on a tissue to be observed, for example an animal's skin. The microbubbles 30 are injected into the bloodstream intravenously.

Sonoporation Process

Figure 5A:
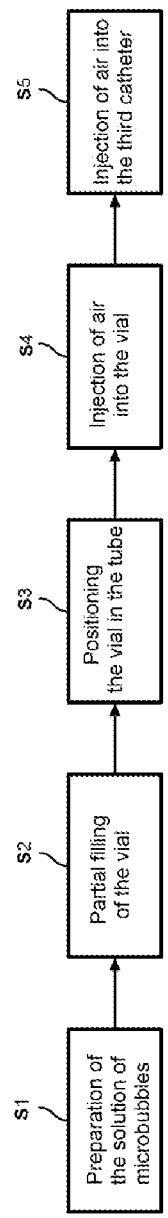
FIG. 5a is a diagram representing a sonoporation process conforming to the invention.

A sonoporation process by means of a device 10 for dispensing microbubbles 30 as described in the previous paragraphs is illustrated in FIG. 5a.

According to a first step S1, the solution 26 containing the microbubbles 30 is prepared. This step S1 comprises the production of anionic or cationic microbubbles 30, the placement of active molecules within these microbubbles 30 and the preparation of the solution 26 containing them.

According to a second step S2, the vial 20 is filled at least partially with the solution 26 containing the microbubbles 30. The vial 20 can be shaken during this step S2. The filling level of the vial 20 may depend on the quantity of active molecules to be transfected, the number of receptacles 61 on the plate 60 and the number of cells to be transfected, the dimensions of the catheters 11, 12, 13, etc.

According to a third step S3, the vial 20 is positioned in the tube 14 of the device 10 for dispensing microbubbles 30 with the head 24 down. The septum of the vial 20 is then pierced by the first and second catheters 11, 12.

According to a fourth step S4, air is injected from the first air injection source. The injected air passes through the first air inlet pipe 16 and the first catheter 11, and opens into the air 25 contained in the vial 20 through the orifice of the first end 111 of the first catheter 11. The volume of air injected is of the order of one microliter. The air thus injected generates an overpressure of the air 25 contained in the vial 20. This overpressure causes the microbubbles 30 contained in the solution 26 to enter the second catheter 12 via the orifice of its first end 121, then to move inside the second catheter 12 toward its second end 122.

According to a fifth step S5, air is injected from the second air injection source. The air passes through the second air inlet pipe 17 and the third catheter 13, which is located around at least part of the second catheter 12. The injected air detaches the microbubbles 30 formed at the second end 122 of the second catheter 12, dispensing them to the cells to be transfected.

Figure 5B:
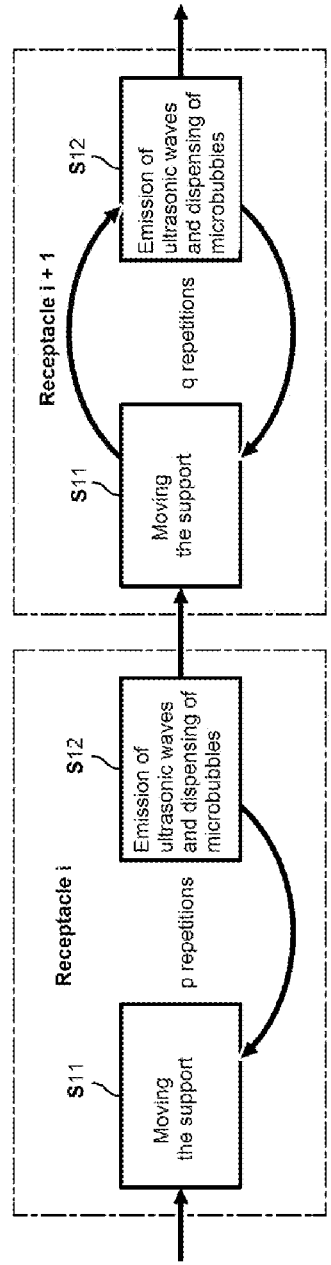
FIG. 5b is a diagram representing a sequence of moving and dispensing of microbubbles conforming to the invention.

A sequence of moving and dispensing of microbubbles 30 by means of a sonoporation device as described in the previous paragraphs is illustrated in FIG. 5b.

According to a first step S11, the support 70 is moved by the moving unit 71, 72 so as to place the geometrical center of a receptacle 61 i of the plate 60, the plate 60 having n receptacles 61, between the ultrasonic transducer 50 and the device 10 for dispensing microbubbles 30 on the vertical axis Z.

According to a second step S12, ultrasonic waves are emitted by the ultrasonic transducer 50 so as to stimulate the center of the receptacle 61 i, while a first proportion of microbubbles 30 is dispensed in the receptacle 61 by the device 10 for dispensing microbubbles 30. The emission of the ultrasonic waves and the dispensing of the microbubbles 30 is stopped after a certain time.

In a variant, the dispensing of microbubbles 30 can be carried out not simultaneously but independently of the emission of the ultrasonic waves, or with a time shift with respect to it.

These steps S11 and S12 can be repeated p times for this receptacle 61 i, according to a desired sequence of moving and dispensing of microbubbles 30: the support 70 is moved so as to place another part of the receptacle 61 i (for example an upper, lower, right or left end of the receptacle 61) between the ultrasonic transducer 50 and the device 10 for dispensing microbubbles 30 on the vertical axis Z, then ultrasonic waves are emitted while a second proportion of the microbubbles 30 is dispensed.

The proportion of microbubbles 30 dispensed in step S12 can be inversely proportional to the number p of times steps S11 and S12 are repeated. For example, in the case where steps S11 and S12 are repeated five times in a moving sequence consisting of first placing the center, then the upper end, then the right end, then the lower end, and finally the left end of receptacle 61 i between the ultrasonic transducer 50 and the device 10 for dispensing microbubbles 30 on the vertical axis Z, the proportion of microbubbles 30 dispensed in each step S12 may correspond to one-fifth of the total quantity of microbubbles 30 to be dispensed in the receptacle 61 i. Thus, at the end of this sequence, the whole quantity of microbubbles 30 to be dispensed in the receptacle 61 i will be dispensed.

Other sequences for moving the receptacle 61 i are of course possible. For example, the support 70 can in step S11 be moved so as to place not the center but one end of the receptacle 61 between the ultrasonic transducer 50 and the device 10 for dispensing microbubbles 30. The sequence of movement of the receptacle 61 can be done in a spiral, or in any other desired pattern. This sequence can be repeated several times for each receptacle 61. The number p of movements of the receptacle 61 may also vary. For example, in the case where the active molecule is a nucleic acid and the amount of nucleic acid to be dispensed into the receptacle 61 i is 1 gram, it can be dispensed by repeating steps S11 and S12 three times and dispensing 0.33 g of nucleic acid at each of the three steps S12.

In a variant, all of the microbubbles 30 can be dispensed at once into the receptacle 61, with the support 70 moving the receptacle 61 i so as to position its center between the ultrasonic transducer 40 and the device 10 for dispensing microbubbles 30 on the vertical axis Z, and all of the microbubbles 30 being dispensed during step S12.

The sequence of moving and dispensing of microbubbles 30 of the receptacle 61 i is completed when the p repetitions of steps S11 and S12 are performed. The support 70 is moved so as to position a receptacle 61 i+1 of the plate 60 between the ultrasonic transducer 40 and the device 10 for dispensing microbubbles 30 on the vertical axis Z. A new sequence of moving and dispensing of microbubbles 30 is then performed. This new sequence of moving and dispensing of microbubbles 30 may consist of a number q of repetitions of steps S11 and S12, where q may be equal to or different from p. Thus, each receptacle 61 benefits from a specific sequence of moving and dispensing of microbubbles 30.

This sequence can be repeated for each of the n receptacles 61 of the plate 60, with the support 70 being moved so as to place each receptacle 61 of the plate 60 successively between the device 10 for dispensing microbubbles 30 and the ultrasonic transducer 50. Thus, the sonoporation operation can be performed on each of the n receptacles 61 containing the cells to be transfected. In a variant, this sequence can be performed only for some of the n receptacles 61 of the plate 60.

The sonoporation process can be executed by a computer program product running on a processor. Such software can communicate with the processing unit in order to automatically control the characteristics of the dispensing of the microbubbles 30 (volume dispensed, position and time of dispensing, time between each dispensed microbubble 30, number of dispensing operations, etc.), the parameters of the ultrasonic waves (frequency, amplitude, power, transmission time, etc.), the movement of the support 70 (directions and speed of movement, position), microbubble the sequences of moving and of dispensing of the microbubbles 30, the opening and closing of the cover 83, etc. Thus, the sonoporation operation can be performed automatically, reproducibly, with specific parameters for each receptacle 61 of the plate 60. The efficiency of such sonoporation is therefore improved compared with current efficiencies.

The sequence of moving and of dispensing of the microbubbles 30 can be predetermined before the sonoporation operation, in which case the user can modify it during the operation via the interface of the processing unit. In a variant, the sequence of moving and of dispensing of the microbubbles 30 can be selected during the operation by the user.

The invention claimed is:

1. A device for dispensing microbubbles for cell sonoporation, wherein the device comprises:
   a tube symmetrical about a vertical axis, said tube being configured to receive a vial containing a solution of microbubbles,
   at least two catheters arranged inside the tube, said catheters being at least partially oriented substantially parallel to the vertical axis, each of the catheters having at a first end an orifice adapted to open into the vial when the latter is received by the tube, the first catheter being adapted to be connected to a first air injection source, the second catheter having a second end,
   wherein, when the first catheter is connected to the first air injection source, air can be injected into the vial via the orifice of the first catheter, the injected air generating an overpressure in the vial, so that microbubbles contained in the vial enter the second catheter via the orifice of its first end, and then move inside the second catheter toward its said second catheter's second end.

2. The device for dispensing microbubbles as claimed in claim 1, further comprising a third catheter at least partially located around at least part of the second catheter, the third catheter being adapted to be connected to a second air injection source.

3. A cell sonoporation device comprising a device for dispensing microbubbles as claimed in claim 1.

4. The cell sonoporation device as claimed in claim 3, further comprising a first air injection source connected to the first catheter, and optionally a second air injection source connected to the third catheter, when the device for dispensing microbubbles comprises a third catheter.

5. The cell sonoporation device as claimed in claim 3, further comprising:
   a tank intended to be at least partially filled with a liquid,
   an ultrasonic transducer arranged inside the tank,
   a plate comprising at least one receptacle intended to receive cells to be transfected,
   a mobile support adapted to receive the plate,
   a mobile support moving unit, configured to move the support.

6. The cell sonoporation device as claimed in claim 5, wherein the moving unit comprises rails extending in at least two dimensions defining a plane perpendicular to the vertical axis, called horizontal plane, the third dimension being that of the vertical axis, the support being intended to be moved along said rails.

7. The cell sonoporation device as claimed in claim 5, wherein the moving unit further comprises a motor adapted to move the support in at least two dimensions defining a plane perpendicular to the vertical axis, called horizontal plane, the third dimension being that of the vertical axis.

8. The cell sonoporation device as claimed in claim 5, wherein the device for dispensing microbubbles is positioned facing the ultrasonic transducer along the vertical axis.

9. The cell sonoporation device as claimed in claim 5, further comprising a housing comprising a first part configured to house the possible air injection sources as well as at least part of the moving unit, the housing further comprising a second part configured to house the device for dispensing microbubbles, the tank, the ultrasonic transducer, the plate and the mobile support, the second part further comprising a cover adapted to be opened or closed, said cover in the open position allowing a user to access at least the plate.

10. The cell sonoporation device as claimed in claim 3, further comprising a processing unit configured to control at least one of the following elements: device for dispensing microbubbles, ultrasonic transducer, moving unit, possible first air injection source and second air injection source, cover.

11. A process for cell sonoporation by means of a device for dispensing microbubbles as claimed in claim 1, a vial containing a solution of microbubbles being received in the device for dispensing microbubbles,
   the sonoporation process comprising a step of injecting air into the vial via the orifice of the first end of the first catheter, the injected air generating an overpressure in the vial, so that microbubbles contained in the vial enter the second catheter via the orifice of its first end and then move inside the second catheter toward its second end.

12. The sonoporation process as claimed in claim 11, further comprising a step of injecting air into a third catheter at least partially located around at least part of the second catheter.

13. The sonoporation process as claimed in claim 11, further comprising a step of moving the support wherein, the device for dispensing microbubbles being positioned facing the ultrasonic transducer along the vertical axis, the support is moved so as to place each receptacle of the plate successively between the device for dispensing microbubbles and the ultrasonic transducer along the vertical axis.

14. A computer program product comprising code instructions for the execution of a sonoporation process as claimed in claim 11 when this program is executed by a processor.

* * * * *